United States Patent [19]
Harris et al.

[11] Patent Number: 5,965,596
[45] Date of Patent: Oct. 12, 1999

[54] METHODS AND COMPOSITIONS FOR INCREASING THE ANAEROBIC WORKING CAPACITY IN TISSUE

[76] Inventors: Roger Harris, 4 Armstrong Close, Newmarket, CB8 8HD, Suffolk, United Kingdom; Mark Dunnett, Chaise House Stables, The Green, Tuddingham, IP 286ST, United Kingdom

[21] Appl. No.: 08/909,513

[22] Filed: Aug. 12, 1997

[51] Int. Cl.⁶ ........................ A61K 31/415; A61K 31/195
[52] U.S. Cl. ............................................. 514/400; 514/561
[58] Field of Search ...................................... 514/400, 561

[56] References Cited

FOREIGN PATENT DOCUMENTS

| | | | |
|---|---|---|---|
| 0 449787 | 10/1991 | European Pat. Off. | A61K 37/02 |
| 3424781 | 1/1985 | Germany | A61K 36/02 |
| 54-159393 | 12/1979 | Japan | A61K 33/44 |
| 3-095125 | 4/1991 | Japan | A61K 37/30 |
| 4-095026 | 3/1992 | Japan | A61K 31/19 |
| 4-112825 | 4/1992 | Japan | A61K 31/19 |
| 6-024976 | 2/1994 | Japan | A61K 31/185 |
| WO 90/06102 | 6/1990 | WIPO | A61K 7/40 |

OTHER PUBLICATIONS

Dunnett, Mark, Carnosine Metabolism and Function in the Thoroughbred Horse (Anaerobic Exercise), *Dissertation* (Open University), vol. 57/04–C of Dissertation Abstracts International, p. 1143, (1996).

Harris, et al., Muscle Buffering Capacity and Dipeptide Content in the Thoroughbred Horse, Greyhound Dog and Man, *Comp. Biochem. Physiol.*, 97A(2):249–251, (1990).

Huszti, et al., "Effects of L–Histidine Administration on the Concentrations of Histidine in Various Tissues", *Agents Actions*, 4(3):183, Aug. (1974).

Nutzenadel, et al., "Uptake and metabolism of β–alanine and L–carnosine by rat tissue in vitro; role in nutrition", *Am. J. of Physiology*, 230(3): 643–51, Mar. (1976).

*Primary Examiner*—Raymond Henley, III
*Attorney, Agent, or Firm*—Fish & Richardson P.C.

[57] ABSTRACT

A method for increasing the synthesis and accumulation of beta-alanylhistidine dipeptides, with a simultaneous increase in the accumulation of creatine, in bodily tissues of humans and animals is described. This is accomplished by causing an increase in the blood plasma concentrations of beta-alanine and creatine, or the blood plasma concentrations of beta-alanine, L-histidine and creatine, by the ingestion or infusion of a composition including beta-alanine, beta-alanine and creatine, or beta-alanine, L-histidine and creatine, or active derivatives thereof.

11 Claims, 13 Drawing Sheets

METHODS AND COMPOSITIONS FOR INCREASING THE ANAEROBIC WORKING CAPACITY IN TISSUE

BACKGROUND OF THE INVENTION

The invention relates to methods and compositions for increasing the anaerobic working capacity of muscle and other tissues.

Natural food supplements are typically designed to compensate for reduced levels of nutrients in the modern human and animal diet. In particular, useful supplements increase the function of tissues when consumed. It can be particularly important to supplement the diets of particular classes of animals whose the normal diet may be deficient in nutrients available only from meat and animal produce (e.g., human vegetarians and other animals consume an herbivorous diet).

For example, in the sporting and athletic community, natural food supplements which specifically improve athletic ability are increasingly important, such as supplements that promote or enhance physical prowess for leisure or employment purposes. In another example, anaerobic (e.g., lactate-producing) stress can cause the onset of fatigue and discomfort that can be experienced with aging. Anaerobic stress can also result from prolonged submaximal isometric exercise when the local circulation is partially or totally occluded by the increase in intra-muscular pressure (e.g., during rock climbing, free diving, or synchronized swimming). Excessive lactate production can result in the acidification of the intracellular environment.

Creatine (i.e., N-(aminoiminomethyl)-N-glycine, N-amidinosarcosine, N-methyl-N-guanylglycine, or methylglycocyamine) is found in large amounts in skeletal muscle and other "excitable" tissues (e.g., smooth muscle, cardiac muscle, or spermatozoa) characterized by a capacity for a high and variable energy demand. Creatine is converted into phosphorylcreatine in energy-generating biochemical pathways within cells. In mammalian skeletal muscle, the typical combined content of creatine (i.e., creatine and phosphorylcreatine) may vary from less than 25 to about 50 mmol per kilogram fresh muscle (i.e., 3.2 to 6.5 grams per kilogram fresh muscle).

Creatine formed is formed in the liver and taken up into tissues, such as muscle, by means of an active transport system. Creatine synthesis in the body may also be augmented by the ingestion of creatine present in meat (e.g., 5–10 milligrams per kilogram body weight per day in the average meat-eating human and approximately zero in a vegetarian diet).

During sustained intensive exercise, or exercise sustained under conditions of local hypoxia, the accumulation of hydronium ions formed during glycolysis and the accumulation of lactate (anaerobic metabolism) can severely reduce the intracellular pH. The reduced pH can compromise the function of the creatine-phosphorylcreatine system. The decline in intracellular pH can affect other functions within the cells, such as the function of the contractile proteins in muscle fibers.

Dipeptides of beta-alanine and histidine, and their methylated analogues, include carnosine (beta-alanyl-L-histidine), anserine (beta-alanyl-L-1-methylhistidine), or balenine (beta-alanyl-L-3-methylhistidine). The dipeptides are present in the muscles of humans and other vertebrates. Carnosine is found in appreciable amounts in muscle of, for example, humans and equines. Anserine and carnosine are found in muscle of, for example, canines, camelids and numerous avian species. Anserine is the predominant beta-alanylhistidine dipeptide in many fish. Balenine is the predominant beta-alanylhistidine dipeptide in some species of aquatic mammals and reptiles. In humans, equines, and camelids, the highest concentrations of the beta-alanylhistidine dipeptides are found in fast-contracting glycolytic muscle fibers (type IIA and IIB) which are used extensively during intense exercise. Lower concentrations are found in oxidative slow-contracting muscle fibers (type I). See, e.g., Dunnett, M. & Harris, R. C. *Equine Vet. J.*, Suppl. 18, 214–217 (1995). It has been estimated that carnosine contributes to hydronium ion buffering capacity in different muscle fiber types; up to 50% of the total in equine type II fibers.

SUMMARY OF THE INVENTION

In general, the invention features methods and compositions for increasing the anaerobic working capacity of muscle and other tissues. The method includes simultaneous accumulation of creatine and beta-alanylhistidine dipeptides, or beta-alanine and L-histidine analogues, within a tissue in the body. The methods include ingesting or infusing compositions into the body. The compositions are mixtures of compounds capable of increasing the availability and uptake of creatine and of precursors for the synthesis and accumulation of beta-alanylhistidine dipeptides, in human and animal muscle. The composition induces the synthesis and accumulation of beta-alanylhistidine dipeptides in a human or animal body when introduced into the body.

The compositions include mixtures of creatine and beta-alanine, creatine, beta-alanine and L-histidine, or creatine and active derivatives of beta-alanine or L-histidine. Each of the beta-alanine or L-histidine can be the individual amino acids, or components of dipeptides, oligopeptides, or polypeptides. The beta-alanine or L-histidine can be active derivatives. An active derivative is a compound derived from, or a precursor of, the substance that performs in the same or similar way in the body as the substance, or which is processed into the substance and placed into the body. Examples include, for example, esters and amides.

In one aspect, the invention features a method of regulating hydronium ion concentrations in a tissue. The method includes the steps of providing an amount of beta-alanine to blood or blood plasma effective to increase beta-alanylhistidine dipeptide synthesis in a tissue, and exposing the tissue to the blood or blood plasma, whereby the concentration of beta-alanylhistidine is increased in the tissue. The method can include the step of providing an amount of L-histidine to the blood or blood plasma effective to increase beta-alanylhistidine dipeptide synthesis.

In another aspect, the invention features a method of increasing the anaerobic working capacity of a tissue. The method includes the steps of providing an amount of beta-alanine to blood or blood plasma effective to increase beta-alanylhistidine dipeptide synthesis in a tissue, providing an amount of L-histidine to the blood or blood plasma effective to increase beta-alanylhistidine dipeptide synthesis in a tissue, and exposing the tissue to the blood or blood plasma. The concentration of beta-alanylhistidine is increased in the tissue.

In embodiments, the methods can include the step of increasing a concentration of creatine in the tissue. The increasing step can include providing an amount of creatine to the blood or blood plasma effective to increase the concentration of creatine in the tissue (e.g., by providing the amount of creatine to the blood or blood plasma).

The providing steps of the methods can include ingestion or infusion (e.g., injection) of a composition including the amount of beta-alanine, or the amounts of beta-alanine and L-histidine, or a combination of ingestion and infusion.

The methods can include increasing a concentration of insulin in the blood or blood plasma. The concentration of insulin can be increased, for example, by injection of insulin.

The tissue can be a skeletal muscle.

In another aspect, the invention features a composition consisting essentially of a peptide source including beta-alanine, between about 39 and about 99 percent by weight of a carbohydrate, and up to about 60 percent by weight of water. The composition includes between about 1 and about 20 percent by weight of the beta-alanine. The peptide source can include L-histidine. The composition can include between about 1 and about 20 percent by weight of L-histidine.

The carbohydrate can be a simple carbohydrate (e.g., glucose). In another aspect, the invention features a composition consisting essentially of a peptide source including beta-alanine, between about 1 and about 98 percent by weight of a creatine source, and up to about 97 percent by weight of water. The composition includes between about 1 and about 98 percent by weight of the beta-alanine. The peptide source can include L-histidine and the composition includes between about 1 and about 98 percent by weight of L-histidine.

The peptide source can be a mixture of amino acids, dipeptides, oligopeptides, polypeptides, or active derivatives thereof.

The composition can be a dietary supplement. The creatine source can be creatine monohydrate.

The concentrations of components in blood or blood plasma can be increased by infusion (i.e., injection) or ingestion of an agent operable to cause an increase in the blood plasma concentration. The composition can be ingested in doses of between about 10 grams and about 800 grams per day. The doses can be administered in one part or multiple parts each day.

An increase in the muscle content of creatine and beta-alanylhistidine dipeptides can increase the tolerance of the cells to the increase in hydronium ion production with anaerobic work, and to lead to an increase in the duration of the exercise before the onset of fatigue. The compositions and methods can contribute to correcting the loss of beta-alanine, L-histidine, or creatine due to degradation or leaching of these constituents during cooking or processing. The compositions and methods can also contribute to correcting the absence of these components from a vegetarian diet.

The methods and compositions can be used to increase beta-alanylhistidine dipeptide by, for example, sportsmen, athletes, body-builders, synchronized swimmers, soldiers, elderly people, horses in competition, working and racing dogs, and game birds, to avoid or delay the onset of muscular fatigue.

Other advantages and features of the invention will be apparent from the detailed description, and from the claims.

DESCRIPTION OF THE PREFERRED EMBODIMENTS

Figure 1:
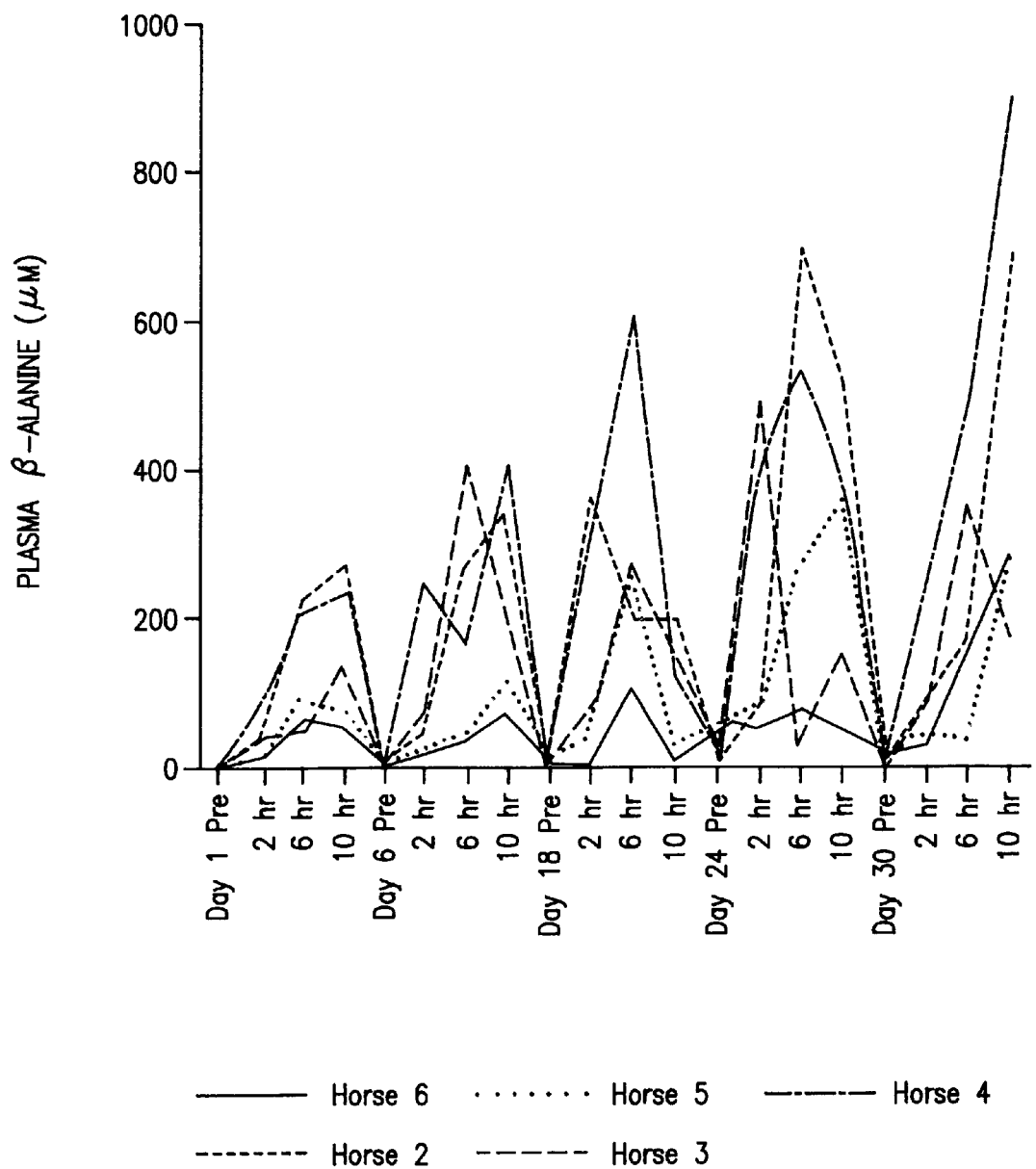
FIG. 1 is a graph depicting changes in the concentrations of beta-alanine in blood plasma of five horses, before and at 2 hour intervals following the feeding of beta-alanine and L-histidine (100 milligrams per kilogram body weight and 12.5 milligrams per kilogram body weight, respectively, three times per day) over a period of 30 days.

Beta-alanylhistidine dipeptides such as carnosine, anserine, and balenine have pKa values between approximately 6.8 and 7.1 and are involved in the regulation of intra-cellular pH homeostasis during muscle contraction and the development of fatigue. The content of other substances involved in hydronium ion buffering, such as amino acid residues in proteins, inorganic and organic phosphates and bicarbonate, is constrained by their involvement in other cell functions. The beta-alanylhistidine dipeptides can provide an effective way of accumulating pH-sensitive histidine residues into a cell. Variations in the muscle beta-alanylhistidine dipeptide concentrations affect the anaerobic work capacity of individual athletes.

The beta-alanylhistidine dipeptides are synthesized within the body from beta-alanine and L-histidine. These precursors can be generated within the body or are made available via the diet, including from the breakdown of an ingested beta-alanylhistidine dipeptide. Beta-alanine within the body is transported to tissues such as muscle. In a typical fed state, the concentration of beta-alanine is low in comparison with the concentration of L-histidine in human and equine blood plasma. These concentrations should be viewed in relation to the affinity of the carnosine synthesizing enzyme, carnosine synthetase, for its substrates as determined by the Michaelis-Menton constant (Km). The Km for histidine is about 16.8 $\mu$M. The Km for beta-alanine is between about 1000 and 2300 $\mu$M. The low affinity of carnosine synthetase for beta-alanine, and the low concentration of beta-alanine in muscle, demonstrate that the concentration of beta-alanine in muscle which is limiting to the synthesis of the beta-alanylhistidine dipeptides.

Increasing the amount of beta-alanylhistidine dipeptides within a muscle favorably affects muscular performance and the amount of work that can be performed by the muscle. Accordingly, the synthesis and accumulation of beta-alanylhistidine dipeptides is increased in a tissue in a human or animal body.

The synthesis and accumulation of beta-alanylhistidine dipeptides in a human or animal body can be increased with an increase in the content within the body of creatine, by increasing the blood or blood plasma concentrations of beta-alanine, increasing the blood or blood plasma concentrations beta-alanine and creatine, or increasing the blood or blood plasma concentrations beta-alanine, L-histidine, and creatine. The increase in dipeptide can be simultaneous with the increase in beta-alanine concentration.

The blood plasma concentrations of beta-alanine, L-histidine and creatine can be increased by ingestion or infusion of beta-alanine, L-histidine, and creatine, or active derivatives thereof. The composition can be administered orally, enterally, or parenterally. The beta-alanine and creatine, or beta-alanine, L-histidine and creatine, are preferably orally ingested.

The composition can include carbohydrates (e.g., simple carbohydrates), insulin, or agents that stimulate the production of insulin.

The composition can be ingested as a dietary supplement. Preferably, the composition can be administered in one or more doses per day. The beta-alanine dosage can be between about 5 milligrams and about 200 milligrams per kilogram body weight. The creatine (e.g., creatine monohydrate) dosage can be between about 5 milligrams to 200 milligrams per kilogram body weight. The L-histidine dosage can be between about 1 milligrams to 100 milligrams per kilogram body weight. The simple carbohydrate (e.g., glucose) dosage can be between about 0.5 and 2.0 grams per kilogram body weight.

In an 80 kilogram person, suitable dosages per day can be between 0.4 grams to 16.0 grams of beta-alanine, 0.4 grams to 16.0 grams of creatine monohydrate, 0.08 grams to 8.0 grams of L-histidine, or 40 grams to 160 grams of glucose or other simple carbohydrate. The composition can be in solid form or liquid form or the form of a suspension which is ingested, or in liquid form or suspension for infusion into the body. The composition is ingested in humans in an amount of between 2 grams and 1000 grams per day (e.g., between 10 grams and 800 grams), which may be taken in one or more parts throughout the day. In animals the daily intake will be adjusted for body weight.

For humans and animals, the compositions can be:
(a) 1% to 99% by weight of beta-alanine;
  1% to 99% by weight of creatine monohydrate; and
  0% to 98% by weight of water;
(b) 1% to 98% by weight of beta-alanine;
  1% to 98% by weight of L-histidine;
  1% to 98% by weight of creatine monohydrate; and
  0% to 97% by weight of water;
(c) 1% to 20% by weight of beta-alanine;
  39% to 99% by weight of glucose or other simple carbohydrate; and
  0% to 60% by weight of water; or
(d) 1% to 20% by weight of beta-alanine;
  1% to 20% by weight of L-histidine
  39% to 99% by weight of glucose or other simple carbohydrate; and
  0% to 60% by weight of water.

The following are specific examples of the methods of methods and compositions for increasing the anaerobic working capacity of muscle and other tissues.

EXAMPLE 1

The effect of supplementation of a normal diet with multiple daily doses of beta-alanine and L-histidine on the carnosine concentration in type I, IIA, and IIB skeletal muscle fibers of thoroughbred horses was assessed. Six experimental thoroughbred horses of normal health (three fillies and three geldings), aged 4 to 9 years, underwent one month (30 days) of dietary conditioning (pre-supplementation period) prior to the commencement of the supplementation period. During the dietary conditioning period each horse was fed a diet comprising 1 kilogram of pelleted feed (Spillers racehorse cubes) and 1 kilogram of soaked sugar beet pulp as a source of complex and simple carbohydrates, three times per day (at 08:30, 12:30, and 16:30, respectively). Soaked hay (3 kilograms dry weight) was also provided twice daily (at 09:00 and 17:00). Water was provided ad libitum.

During the supplementation period an identical feeding regime was implemented. However, each hard feed meal was supplemented with beta-alanine and L-histidine (free base). Beta-alanine and L-histidine were mixed directly into the normal feed. Individual doses of beta-alanine and L-histidine were calculated according to body weight. Beta-alanine was administered at 100 milligrams per kilogram body weight and L-histidine at 12.5 milligrams per kilogram body weight. Dietary supplementation was begun on day 1 of the protocol and discontinued at the end of day 30. Heparinized blood samples (5 milliliters) were collected on days 1, 6, 18, 24, and 30. On day 1 and day 30, blood samples were collected prior to the first feed and at hourly intervals for a total of 12 hours each day. On the three intervening sampling days, blood was collected prior to the first feed and 2 hours after each subsequent feed. On the day before the start of supplementation (day 0) a muscle biopsy was taken, following application of local anaesthesia of the skin, from the right middle gluteal muscle (m. gluteus medius) of each horse using a Bergstrom-Stille percutaneous biopsy needle. Subsequent muscle biopsies were collected immediately after the end of the supplementation period (day 31) as close as possible to the original sampling site. Clinical monitoring of the horses was performed daily. This comprised a visual examination and measurement of body weight, twice-daily measurement of rectal temperature, and weekly blood sampling for clinical biochemistry and hematology. During the course of the study the horses received no formal training or exercise, although they were allowed one hour of free exercise each day.

Fragments of individual muscle fibers dissected from freeze-dried muscle biopsies were characterized as either type I, IIA or IIB by histochemical staining for myosin ATPase activity at pH 9.6 following pre-incubation at pH 4.50 by a modification of the method described in, Kaiser and Brook, *Arch. Neurol.*, 23:369–379 (1970).

Heparinized blood plasma samples were extracted and analyzed for beta-alanine and L-histidine concentrations by high-performance liquid chromatography (HPLC). Individual weighed muscle fibers were extracted and analyzed for carnosine by HPLC according to the method described in, Dunnett and Harris, "High-performance liquid chromatographic determination of imidazole dipeptides, histidine, 1-methylhistidine and 3-methylhistidine in muscle and individual muscle fibers," *J. Chromatogr. B. Biomed. Appl.*, 688:47–55 (1997).

Differences in carnosine concentrations within fiber types before and after supplementation were established within horses using one-way analysis of variance (ANOVA). In instances where differences were detected, significance was determined using a multiple comparison test (Fisher's PLSD).

No palatability problems were encountered with the addition of beta-alanine and L-histidine to the feed. No adverse physiological or behavioral effects of the supplemented diet were observed in any of the horses during the thirty days of supplementation. No significant changes in body weight were recorded, and rectal temperatures remained within the normal range. No acute or chronic changes in clinical biochemistry or hematology were observed. Beta-alanine was not detected in the plasma of any of the horses prior to the start of supplementation. The lower limit of quantitation for beta-alanine in plasma by the assay used was 3 micromolar ($\mu$M). Plasma L-histidine concentrations in the six horses prior to the start of supplementation were between 36.6 and 54.4 $\mu$M.

Figure 2:
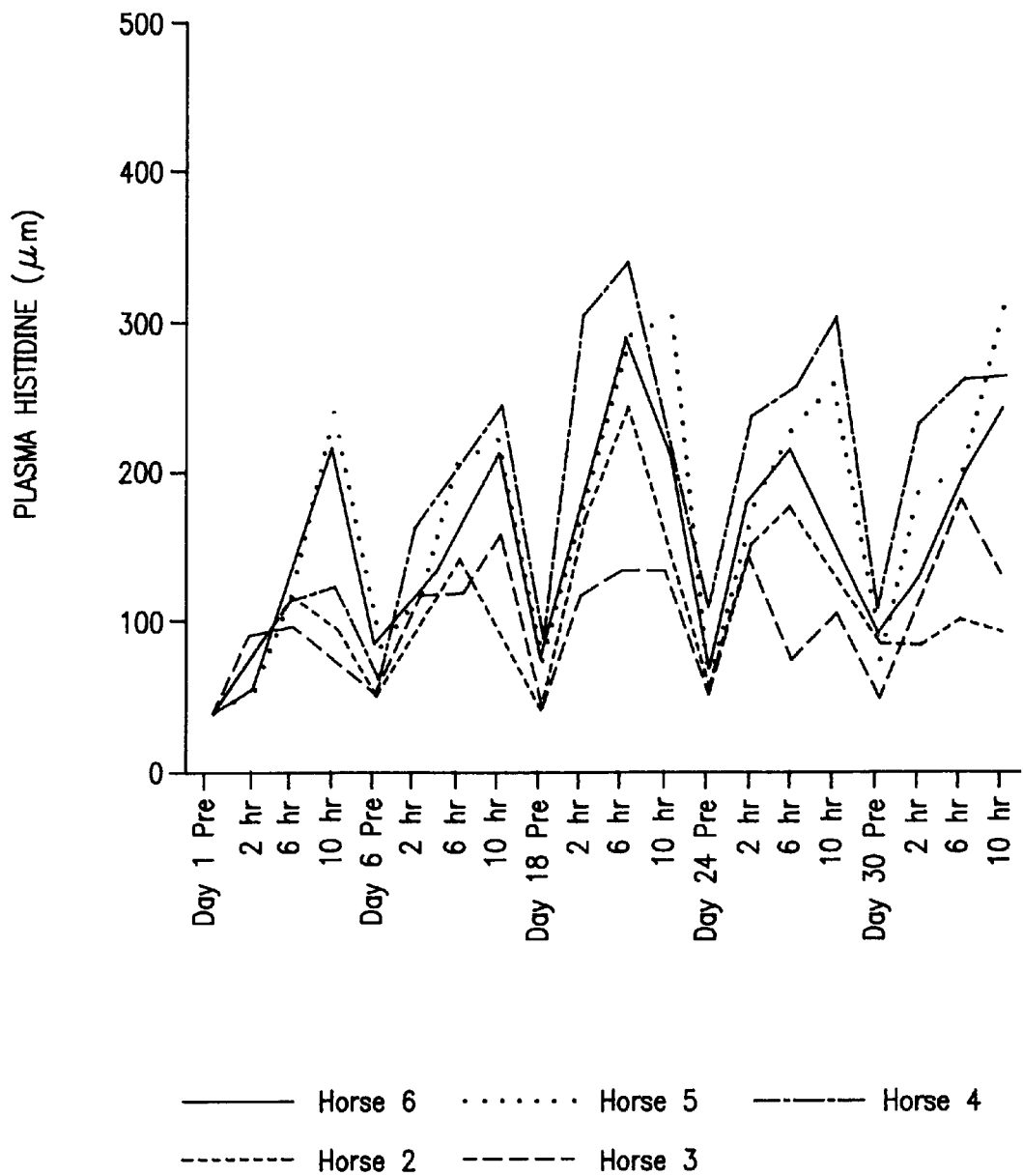
FIG. 2 is a graph depicting changes in the concentrations of L-histidine in blood plasma of five horses, before and at 2 hour intervals following the feeding of beta-alanine and L-histidine (100 milligrams per kilogram body weight and 12.5 milligrams per kilogram body weight, respectively, three times per day) over a period of 30 days.
Figure 3A:
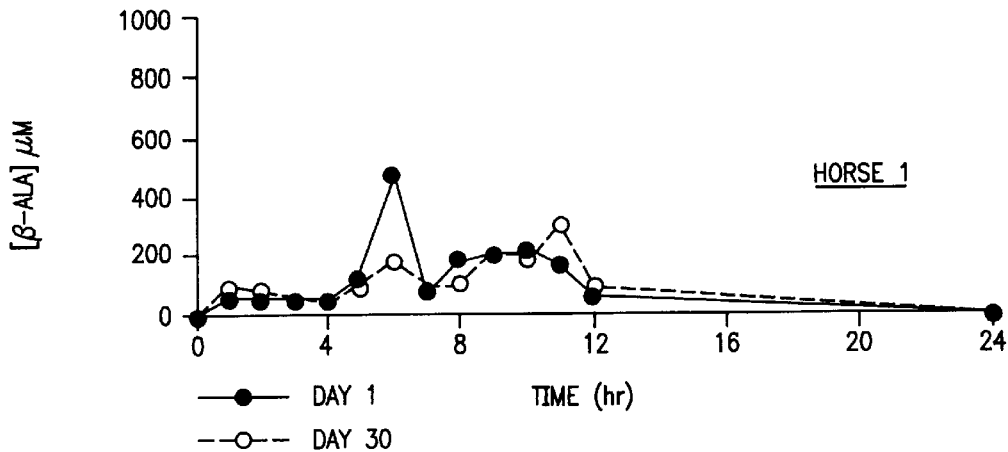
FIGS. 3a and 3b are graphs depicting the contrast in the changes in the concentrations of beta-alanine in blood plasma of six horses, before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation.
Figure 3B:
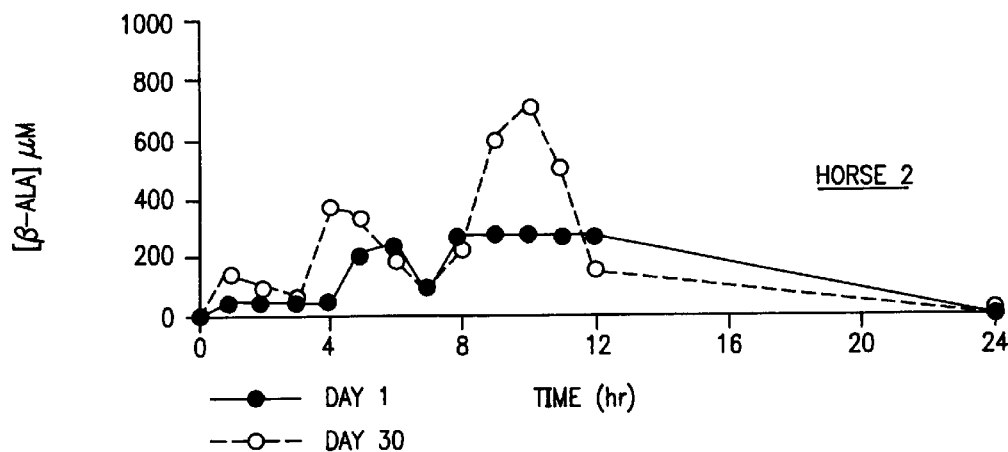
Figure 3C:
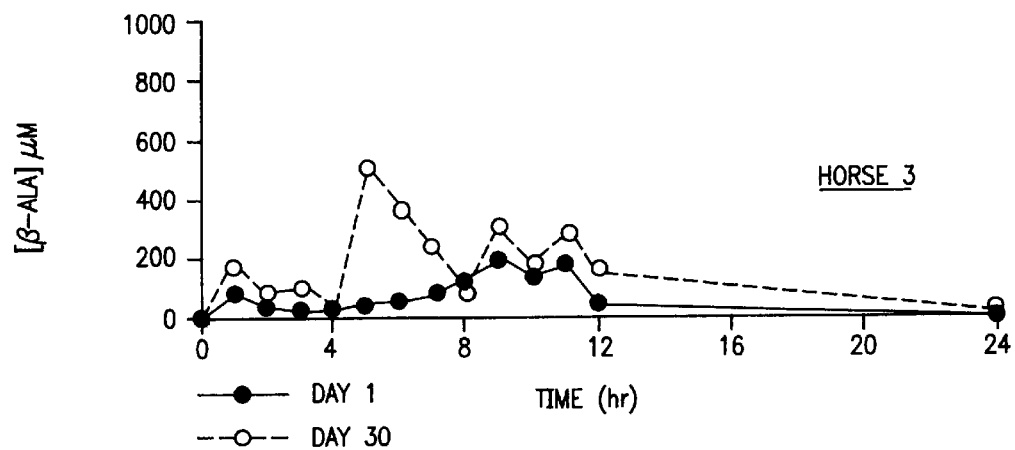
Figure 3D:
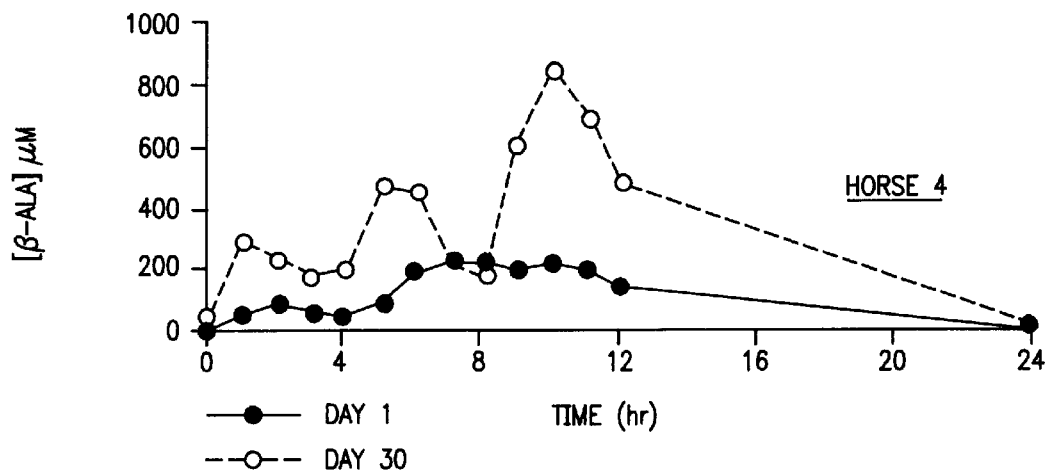
Figure 3E:
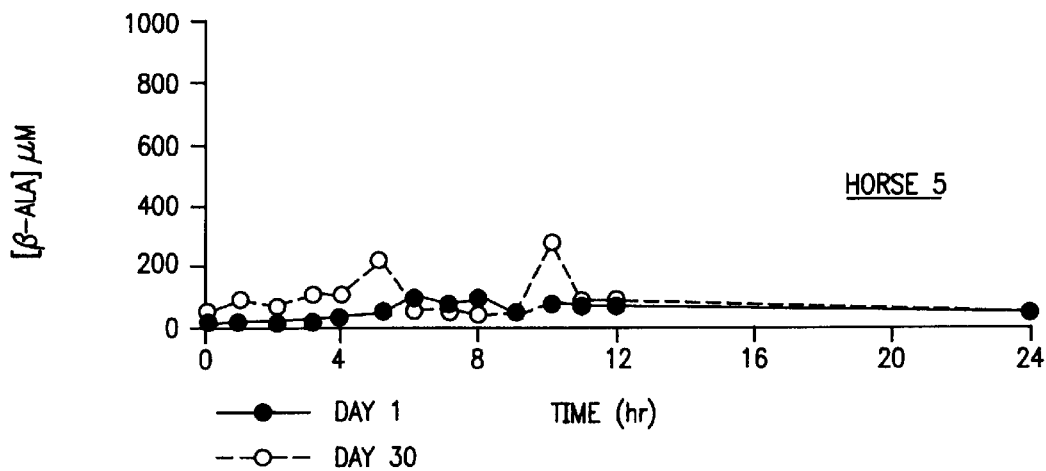
Figure 3F:
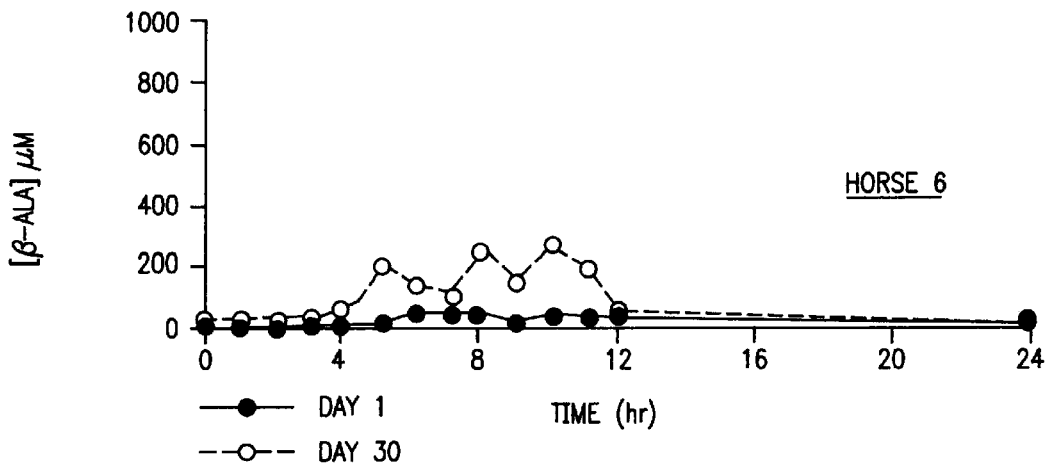
Figure 4A:
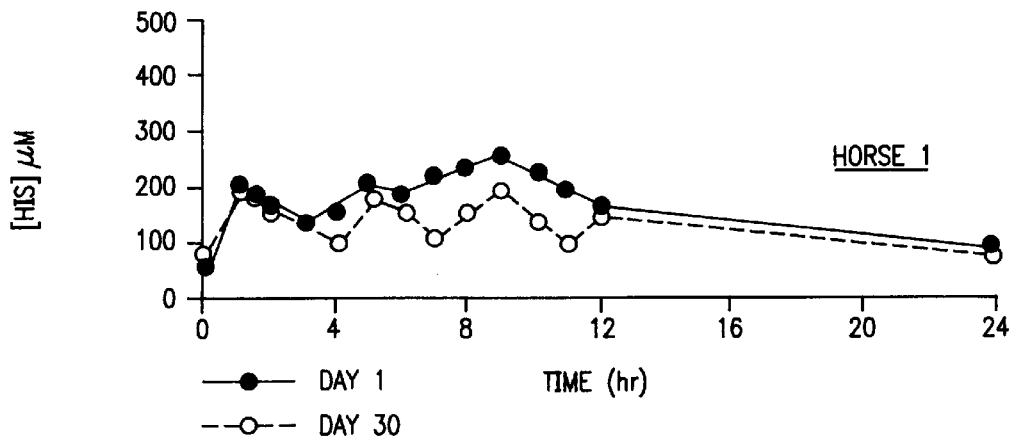
FIGS. 4a and 4b are graphs depicting the contrast in the changes in the concentrations of L-histidine in blood plasma of six horses, before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation.
Figure 4B:
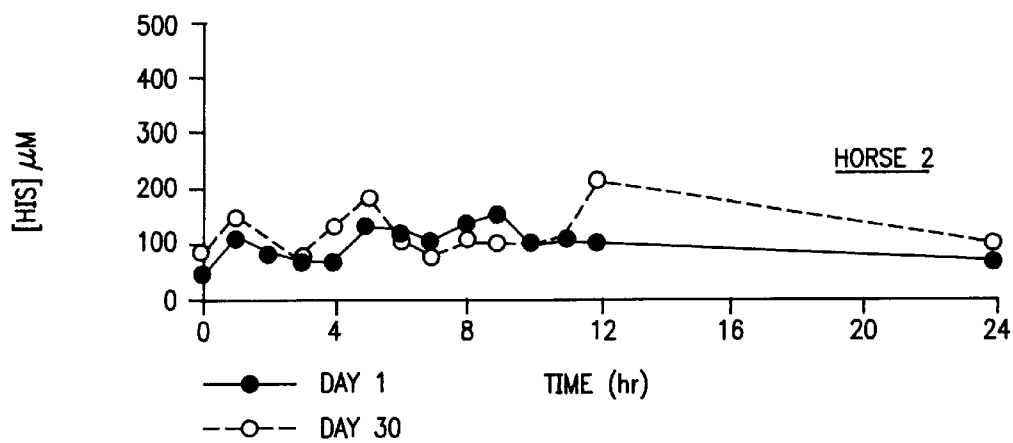
Figure 4C:
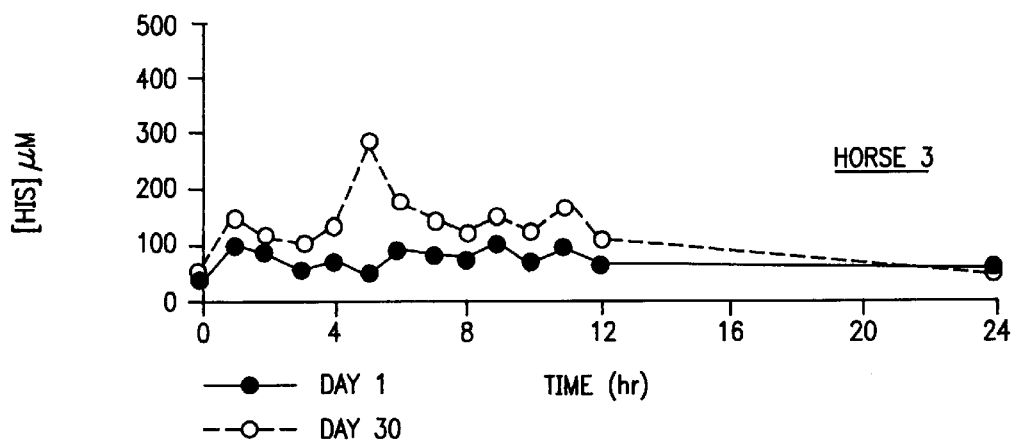
Figure 4D:
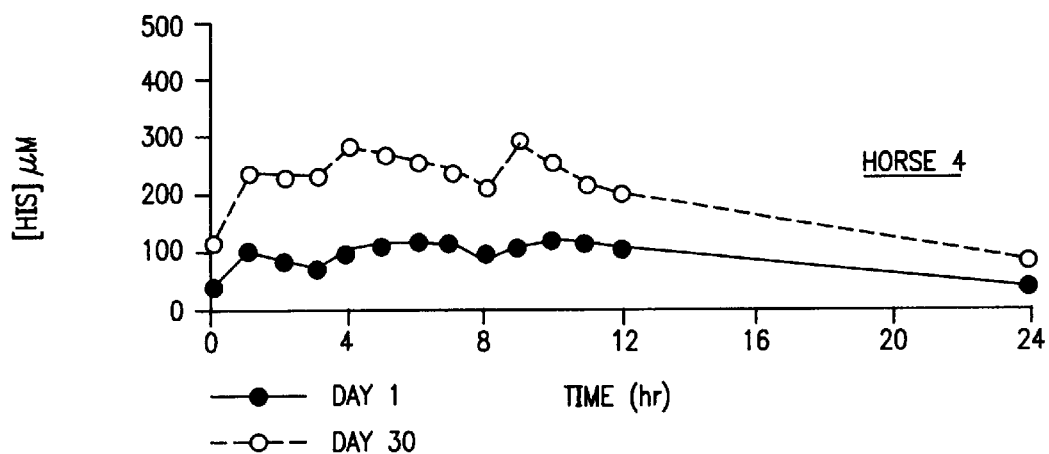
Figure 4E:
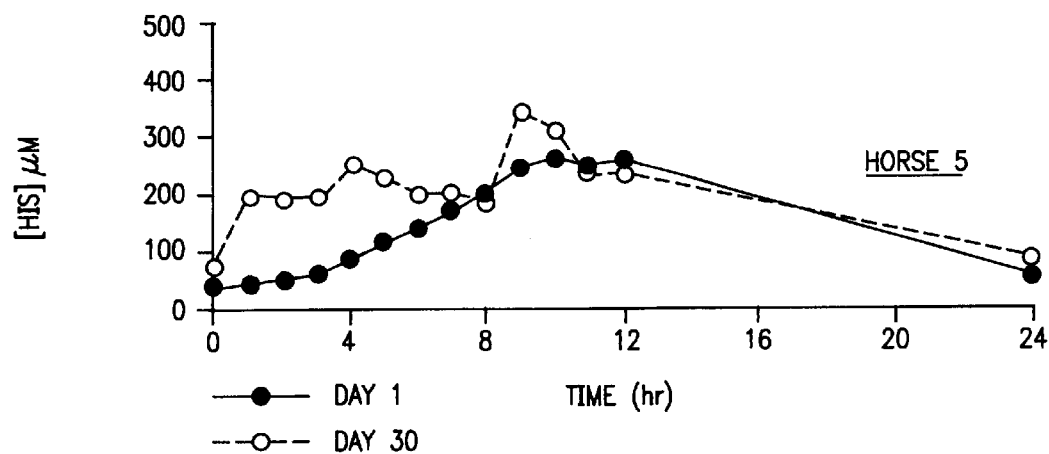
Figure 4F:
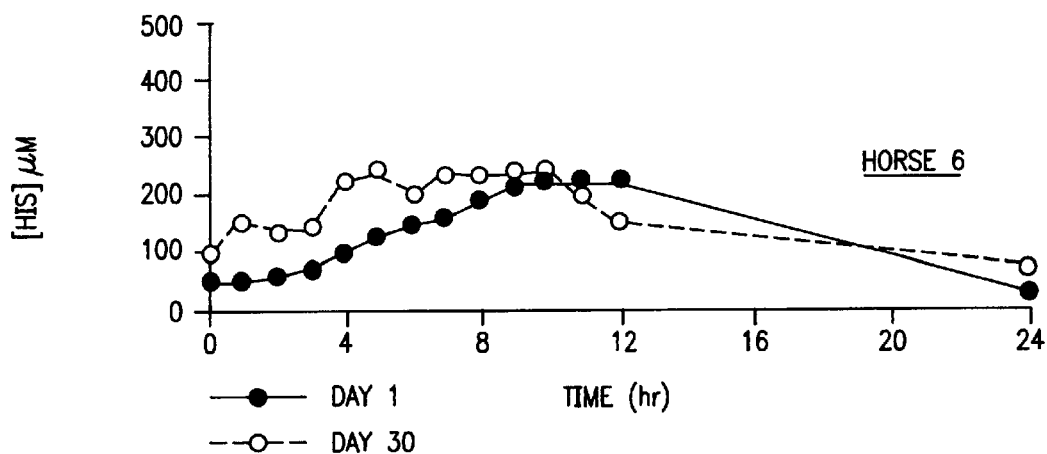

Individual changes in blood plasma beta-alanine and L-histidine concentrations for five of the six horses over on all the sampling days are shown in FIGS. 1 and 2, respectively. There was a trend towards an increase in the pre-feeding concentrations of blood plasma beta-alanine and L-histidine with increasing time of supplementation. Furthermore, over the thirty day supplementation period, the blood plasma concentration response to supplementation was also increased. The response was greater for beta-alanine.

Figure 5:
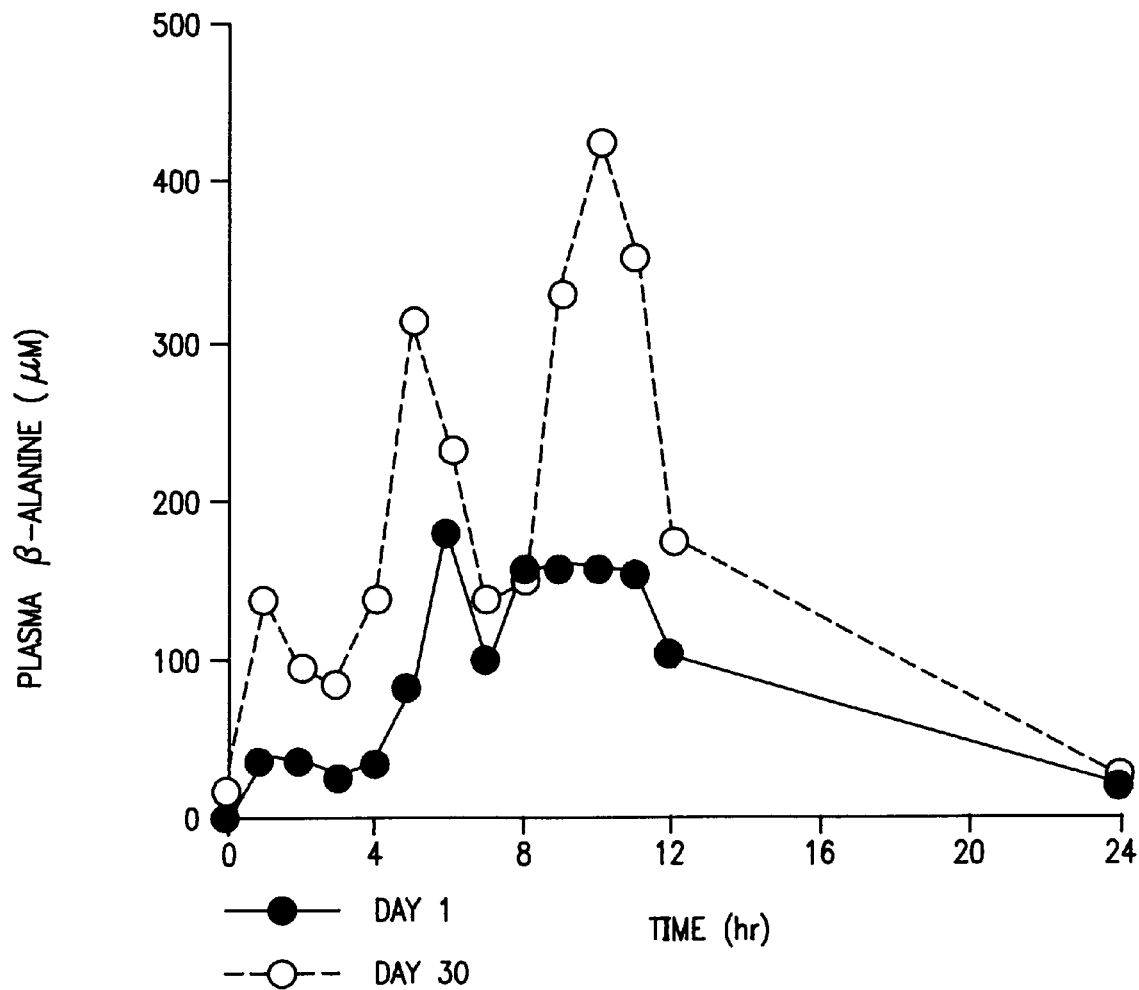
FIG. 5 is a graph depicting the contrast in the changes in the mean concentrations of beta-alanine in equine blood plasma (n=6), before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation.

Comparisons of the changes in blood plasma beta-alanine and L-histidine concentrations prior to the first feed of the day, and hourly thereafter between the first and last days of the supplementation period, for the six individual horses, are shown in FIGS. 3a and 3b, and FIGS. 4a and 4b, respectively. The mean (±SD) changes (n=6) in blood plasma beta-alanine concentration over time during the 24 hours of the first (day 1) and last (day 30) days of the supplementation period are contrasted in FIG. 5. The area under the mean blood plasma beta-alanine concentration versus time curve over 24 hours ($AUC_{(0-24\ hr)}$) was much greater on day 30 of the supplementation.

Figure 6:
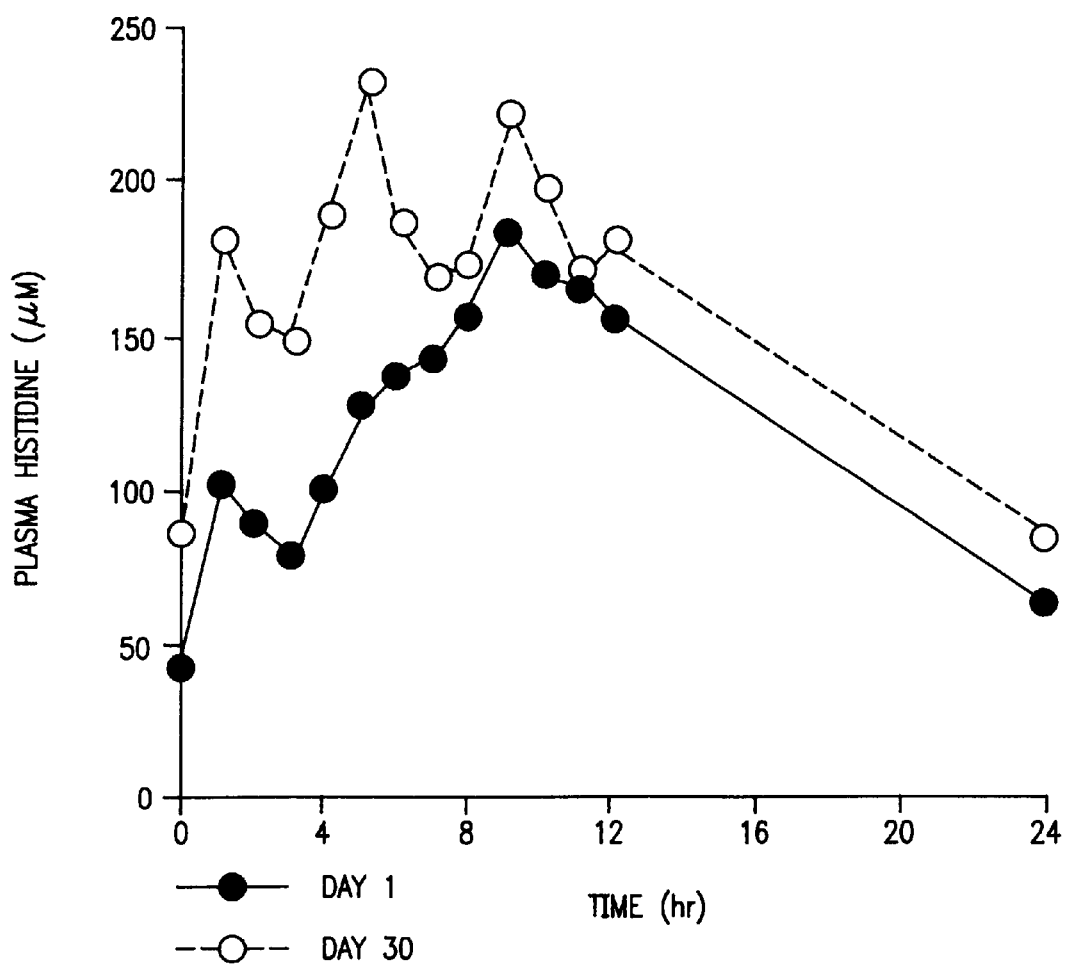
FIG. 6 is a graph depicting the contrast in the changes in the mean concentrations of L-histidine in equine blood plasma (n=6), before and at hourly intervals following the feeding of beta-alanine and L-histidine (100 milligrams per kilogram body weight and 12.5 milligrams per kilogram body weight, respectively, three times per day) on the first and last day of a 30 day period of dietary supplementation.

The mean (±SD) changes (n=6) in blood plasma L-histidine concentration over time during the 24 hours of the first (day 1) and last (day 30) days of the supplementation period are contrasted in FIG. 6. The area under the mean blood plasma beta-alanine concentration vs. time curve over 24 hours ($AUC_{(0-24\ hr)}$) was greater on day 30 of the supplementation. The greater AUC for blood plasma beta-alanine on the last day of supplementation (day 30) in contrast to the first day of supplementation (day 1) suggests the increased uptake of beta-alanine from the equine gastrointestinal tract with progressive supplementation. A similar effect was observed for changes in blood plasma L-histidine concentration during the supplementation period. Peak blood plasma concentrations of beta-alanine and L-histidine occurred approximately one to two hours post-feeding in each case.

A total of 397 individual skeletal muscle fibers (192 pre-supplementation; 205 post-supplementation) from the six horses were dissected and analyzed for carnosine. Mean (±SD) carnosine concentration, expressed as millimoles per kilogram dry weight (mmol kg$^{-1}$ dw), in pre- and post-supplementation type I, IIA, and IIB skeletal muscle fibers from the six individual horses are given in Table 1 where n is the number of individual muscle fibers analyzed. Following thirty days of beta-alanine and L-histidine supplementation the mean carnosine concentration was increased in type IIA and IIB fibers in all six horses. These increases were statistically significant in seven instances. The increase in mean carnosine concentration in type IIB skeletal muscle fibers was statistically significant in five out of six horses. The increase in mean carnosine concentration in type IIA skeletal muscle fibers was statistically significant in two out of six horses.

TABLE 1

| Horse | Day | Type 1 | n | Type IIA | n | Type IIB | n |
|---|---|---|---|---|---|---|---|
| 6 | 0 | 32.3 (14.5) | 3 | 72.1 (47.7) | 11 | 111.8 (22.8) | 14 |
|   | 31 | — |   | 16.2 (20.9) | 17 | 117.7 (38.7) | 12 |
| 5 | 0 | 59.5 (3.9) | 2 | 102.6 (12.7) | 12 | 131.2 (26.6) | 26 |
|   | 31 | 55.5 | 1 | 112.2 (17.1) | 18 | 153.3 (28.0)** | 22 |
| 4 | 0 | 44.8 (6.6) | 4 | 59.9 (19.52) | 13 | 108.6 (41.5) | 19 |
|   | 31 | 37.0 (9.3) | 2 | 88.0 (34.2)* | 17 | 152.4 (65.0)* | 19 |
| 1 | 0 | 56.7 (5.3) | 2 | 88.5 (20.9) | 15 | 101.3 (15.2) | 13 |
|   | 31 | 57.8 | 1 | 96.1 (17.3) | 19 | 14.3 (13.3)* | 11 |
| 2 | 0 | — |   | 89.6 (16.2) | 13 | 104.2 (22.2) | 14 |
|   | 31 | 65.9 (13.2) | 4 | 102.2 (22.1) | 18 | 142.0 (35.4)*** | 12 |
| 3 | 0 | 30.9 (4.0) | 2 | 85.1 (20.3) | 6 | 113.5 (20.4) | 23 |
|   | 31 | — |   | 105.0 (17.6)* | 23 | 135.4 (24.9)* | 9 |
| Mean | 0 | 44.8 | 13 | 83.0 | 70 | 111.8 | 109 |
|   | 31 | 54.1 | 8 | 96.6* | 112 | 135.9** | 85 |

*significantly different to pre-supplementation, p < 0.05
**significantly different to pre-supplementation, p < 0.01
***significantly different to pre-supplementation, p < 0.005

The absolute (e.g. mmol kg$^{-1}$ dw) and percentage increases in the mean carnosine concentrations in type IIA and IIB skeletal muscle fibers from the six horses are listed in Table 2.

TABLE 2

| Horse | Type IIA Absolute increase | Type IIA % increase | Type IIB Absolute increase | Type IIB % increase |
|---|---|---|---|---|
| 6 | 4.1 | 5.7 | 5.6 | 5.3 |
| 5 | 9.6 | 9.4 | 22.1 | 16.8 |
| 4 | 28.1 | 46.9 | 43.8 | 40.3 |
| 1 | 7.6 | 8.6 | 13.0 | 12.8 |
| 2 | 12.6 | 14.1 | 37.8 | 36.3 |
| 3 | 19.9 | 23.4 | 21.9 | 19.3 |
| Mean | 13.6 | 18.0 | 24.1 | 21.8 |

Figure 7:
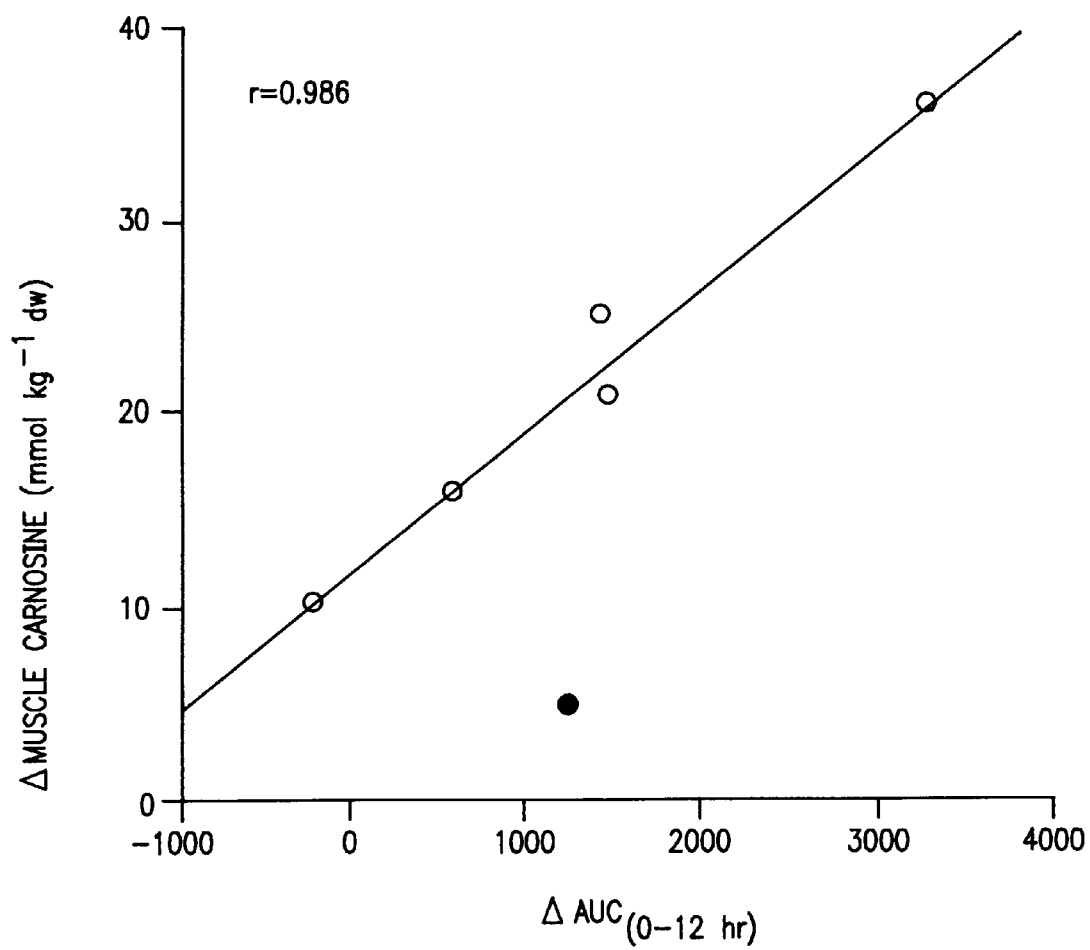
FIG. 7 is a graph depicting the correlation between the increase in 6 thoroughbred horses in the carnosine concentration in type II skeletal muscle fibers (the average of the sum of type IIA and IIB fibres) and the increase, between the 1st and 30th day of supplementation, in the area under the blood plasma beta-alanine concentration-time curve over the first 12 hours of the day ($AUC_{(0-12\ hr)}$).

It was observed that the individual horses which showed the greater increase in muscle carnosine concentration following thirty days of supplementation also demonstrated the greater increase in blood plasma beta-alanine AUC between day 1 and day 30 of the supplementation period. Referring to FIG. 7, a significant correlation ($r=0.986$, $p<0.005$) for five of the six horses was observed between the increase in mean carnosine concentration, averaged between type IIA and IIB skeletal muscle fibers and the increase, between the 1st and 30th day of supplementation, in blood plasma beta-alanine AUC, over the first 12 hours ($AUC_{(0-12)}$) Only five horses were used to calculate the regression line. Horse 6 (filled circle) showed no appreciable increase in blood plasma beta-alanine concentration greater than that observed on day 1 until the last day of supplementation. This was unlike the other five horses which showed a progressive increase with each sampling day. For this reason horse 6 was excluded from the calculation of the regression equation.

Increases in muscle carnosine concentration following thirty days of supplementation with beta-alanine and L-histidine will cause a direct increase in total muscle buffering capacity. This increase can be calculated by using the Henderson-Hasselbach Equation. Calculated values for the increases in muscle buffering capacity in type IIA and IIB skeletal muscle fibers in the six thoroughbred horses are shown in Table 3.

beta-alanine in six normal subjects following the consumption of a broth delivering approximately 40 milligrams per kilogram body weight of beta-alanine was monitored. Doses of 10 and 20 milligrams per kilogram body weight of beta-alanine were also given.

The broth was prepared as follows. Fresh chicken breast (skinned and boned) was finely chopped and boiled for fifteen minutes with water (1 liter for every 1.5 kg of chicken). Residual chicken meat was removed by course filtration. The filtrate was flavored by the addition of carrot, onion, celery, salt, pepper, basil, parsley and tomato puree, and reboiled for a further fifteen minutes and then cooled before final filtration though fine muslin at 4° C. The yield from 1.5 kilograms of chicken and one liter of water was 870 mL of broth. A portion of the stock was assayed for the total beta-alanyl-dipeptide content (e.g., carnosine and anserine) and beta-alanine. Typical analyses were:

| total beta-alanyl-dipeptides | 74.5 mM |
|---|---|
| free beta-alanine | 5.7 mM |

The six male test subjects were of normal health and between 25–53 years of age, as shown in Table 4. The study commenced after an overnight fast (e.g., a minimum of 12 hours after the ingestion of the last meat containing meal). Subjects were given the option to consume a small quantity of warm water prior to the start of the study. Catheterization was begun at 08:30 and the study started at 09:00.

As a control, 8 milliliters per kilogram body weight of water was ingested (e.g., 600 mL in a subject weighing 75 kilograms).

In one session, 8 milliliters per kilogram body weight of broth containing approximately 40 milligrams per kilogram body weight of beta-alanine (e.g., in the form of anserine and carnosine) was ingested. For a subject weighing 75 kilograms this amounted to the ingestion of 600 milliliters of broth containing 3 grams of beta-alanine. In another session, 3 milliliters per kilogram body weight of a liquid containing the test amount of beta-alanine with an additional 5 milliliters per kilogram body weight of water was ingested. In all sessions, subjects additionally consumed a further 8 milli-

TABLE 3

| Horse | Day | Type IIA βmcar | Type IIA βmtotal | Type IIA Δβmtotal (%) | Type IIB βmcar | Type IIB βmtotal | Type IIB Δβmtotal (%) |
|---|---|---|---|---|---|---|---|
| 6 | 0 | 23.9 | 93.9 | | 37.1 | 107.1 | |
|   | 31 | 25.3 | 95.3 | +1.5 | 39.0 | 109.0 | +1.8 |
| 5 | 0 | 34.0 | 104.0 | | 43.5 | 113.5 | |
|   | 31 | 37.2 | 107.2 | +3.1 | 50.8 | 120.8 | +6.4 |
| 4 | 0 | 19.9 | 89.9 | | 36.0 | 106.0 | |
|   | 31 | 29.2 | 99.2 | +10.3 | 50.5 | 120.5 | +13.7 |
| 1 | 0 | 29.3 | 99.3 | | 33.6 | 103.6 | |
|   | 31 | 31.9 | 101.9 | +2.6 | 37.9 | 107.9 | +4.2 |
| 2 | 0 | 29.7 | 99.7 | | 34.5 | 104.5 | +12.1 |
|   | 31 | 33.9 | 103.9 | +4.2 | 47.1 | 117.1 | |
| 3 | 0 | 28.2 | 98.2 | | 37.6 | 107.6 | |
|   | 31 | 34.8 | 104.8 | +6.7 | 44.9 | 114.9 | +6.8 |
| Mean | 0 | 27.5 | 97.5 | | 37.1 | 107.1 | |
|   | 31 | 32.1 | 102.1 | +4.7 | 45.0 | 115.0 | +7.5 |

EXAMPLE 2

The effect of supplementation of a normal diet with multiple daily doses of beta-alanine and L-histidine on the carnosine content of type I, IIA, and IIB skeletal muscle fibers of humans was assessed. The plasma concentration of liters per kilogram body weight of water (in 50 mL portions) during the period of 1 to 2 h after ingestion. A vegetarian pizza was provided after 6 hours. An ordinary diet was followed after 8 hours.

2.5 milliliter venous blood samples were drawn through an indwelling catheter at 10 minute intervals for the first 90 minutes and then after 120, 180, 240 and 360 minutes. The blood samples were dispensed into tubes containing lithium-heparin as anti-coagulant. The catheter was maintained by flushing with saline. Plasma samples were analyzed by HPLC according to the method described in Jones & Gilligan (1983) *J. Chromatogr.* 266:471–482 (1983).

Table 4 summarizes the allocation of treatments during the beta-alanine absorption study. The estimated equivalent doses of beta-alanine are presented in Table 3.

study. On each of these three test days subjects were catheterized and an initial blood sample taken when the beta-alanine was administered at or close to 9 am, 12 noon, and 3 pm. Blood samples were drawn after 30, 60, 120 and 180 minutes, and analyzed for changes in the plasma concentration of beta-alanine and taurine. 24 hour urine samples were collected over each day of the study and analyzed by HPLC to determine the excretion of beta-alanine and taurine. The treatments are summarized in Table 5.

TABLE 4

| Subject | Age yrs | Weight kg | Broth 40 mg/kg bwt | β-ala 0 mg/kg bwt | β-ala 10 mg/kg bwt | β-ala 20 mg/kg bwt | β-ala 40 mg/kg bwt | Carnosine 20 mg/kg bwt |
|---|---|---|---|---|---|---|---|---|
| 1 | 53 | 76 | ✓ | | | ✓ | ✓ | ✓ |
| 2 | 33 | 60 | ✓ | | | ✓ | ✓ | |
| 3 | 29 | 105 | ✓ | ✓ | ✓ | ✓ | | |
| 4 | 31 | 81 | ✓ | ✓ | ✓ | | ✓ | |
| 5 | 30 | 94 | ✓ | ✓ | ✓ | | ✓ | |
| 6 | 25 | 65 | ✓ | ✓ | ✓ | ✓ | | |

Figure 8:
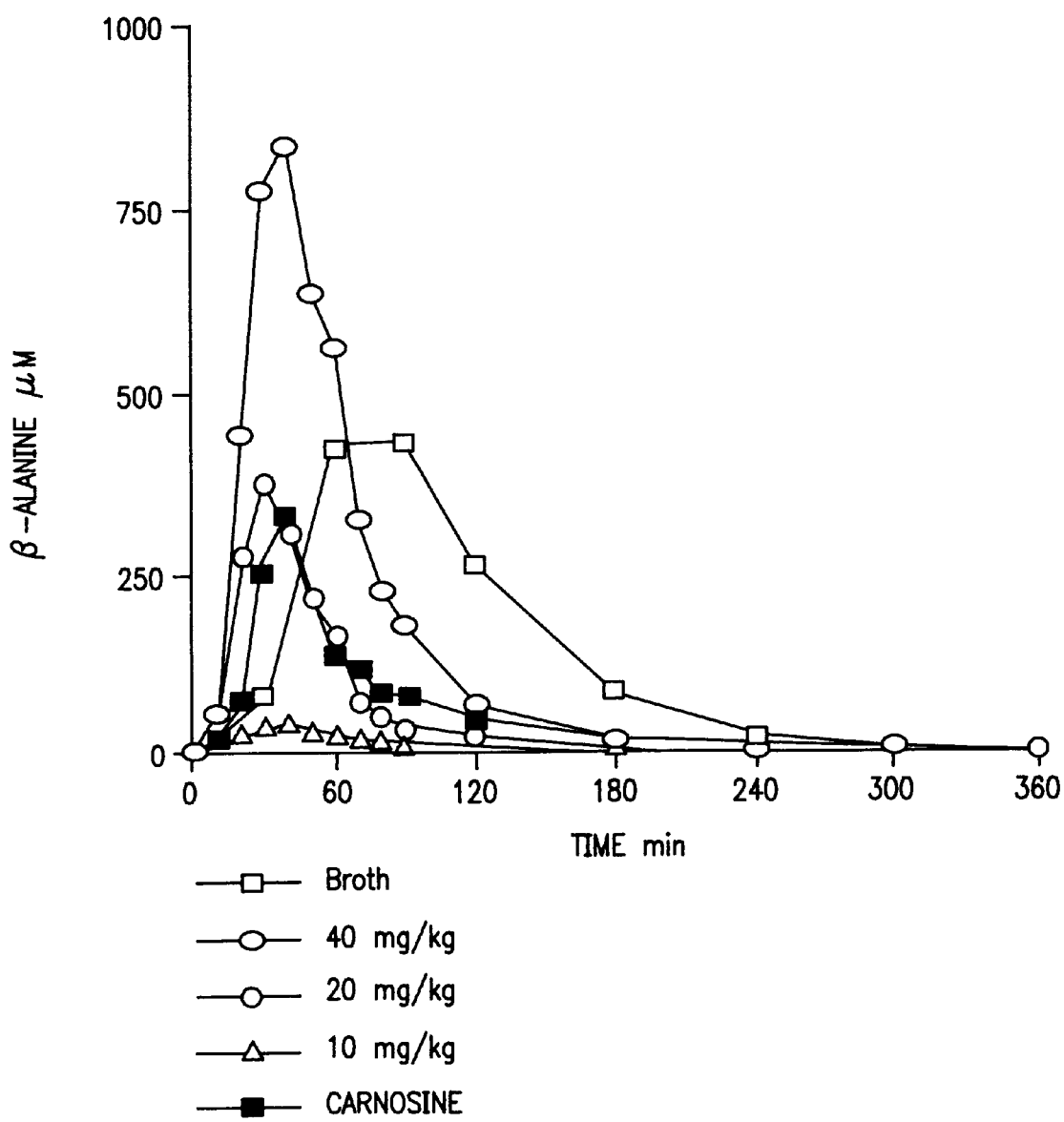
FIG. 8 is graph depicting the mean results of the administration of beta-alanine, broth, or carnosine to test subjects.

Plasma concentration curves following each treatment are depicted graphically in FIG. 8. Mean results of the administration of beta-alanine, broth, or carnosine according to the treatments schedule in Table 4. Plasma beta-alanine was below the limit of detection in all subjects on the control treatment. Neither carnosine or anserine were detected in plasma following ingestion of the chicken broth or any of the other treatments. Ingestion of the broth resulted in a peak concentration in plasma of 427.9 (SD 161.8) $\mu$M. Administration of carnosine equivalent to 20 milligrams per kilogram body weight of beta-alanine in one test subject resulted in an equivalent increase in the plasma beta-alanine concentration.

Administration of all treatments except control resulted in an increase in the plasma taurine concentration. The changes in taurine concentration mirrored closely those of beta-alanine. Administration of broth, a natural food, caused the an equivalent increase in plasma taurine, indicating that such a response is occurring normally following the ingestion of most meals.

EXAMPLE 3

The effect of administration of three doses of 10 milligrams per kilogram body weight of beta-alanine per day (i.e., administered in the morning, noon, and at night) for seven days on the plasma concentration profiles of beta-alanine and taurine were investigated. The plasma concentration profiles following administration of 10 milligrams per kilogram body weight of beta-alanine were studied in three subjects at the start and end of a seven day period during which they were given three doses of the beta-alanine per day.

Three male subjects of normal health, aged between 33–53 years were studied. Test subjects received three doses per day of 10 milligrams per kilogram body weight of beta-alanine for eight days. In two subjects, this was followed by a further 7 days (days 9–15) when three doses of 20 milligrams per kilogram body weight per day were given. Subjects reported at 8 am to the blood collection laboratory on days 1 (prior to any treatment given), 8 and 15 following an overnight fast. Subjects were asked not to consume any meat containing meal during the 12 hours preceeding the

TABLE 5

| Treatment Day beta-alanine | Day 1 10 mg/kg bwt | Day 8 10 mg/kg bwt | Day 15 20 mg/kg bwt |
|---|---|---|---|
| 1 | ✓ | ✓ | ✓ |
| 2 | ✓ | ✓ | ✓ |
| 3 | ✓ | ✓ | |

Figure 9:
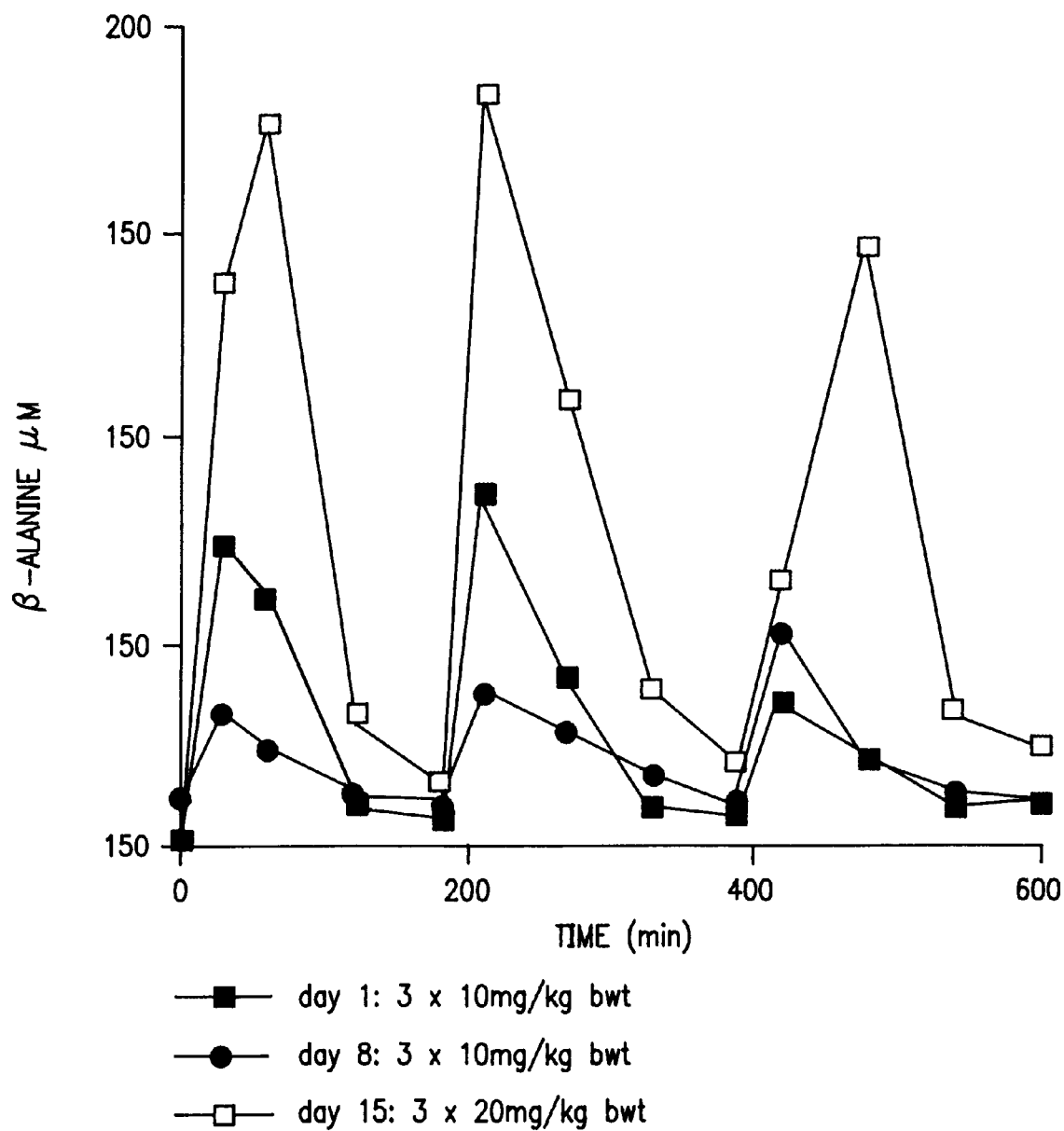
FIG. 9 is a graph depicting mean changes in plasma beta-alanine over nine hours of treatment.

The plasma beta-alanine concentrations are summarized in FIG. 9. Each dose resulted in a peak beta-alanine concentration at one-half hour or one hour after ingestion followed by a decline to a 0–10 micromolar basal level at three hours, just prior to administration of the next dose. The response on day 8 of the treatment tended to be less than on day 1 as indicated by the area under the plasma concentration curve.

EXAMPLE 4

The effect of administration of three doses of 40 milligrams per kilogram body weight of beta-alanine per day (i.e., administered in the morning, noon, and at night) for 2 weeks on the carnosine content of muscle, and isometric endurance at 66% of maximal voluntary contraction force.

Six normal male subjects, aged 25 to 32 years, that did not have evidence of metabolic or muscle disease were recruited into the study. The subjects were questioned regarding their recent dietary and supplementary habits. None of subjects was currently taking supplements containing creatine, or had done so in recent testing supplementation procedures. The physical characteristics of the test subjects are summarized in Table 6.

TABLE 6

| Subject | Age (years) | Weight (kg) |
|---|---|---|
| 1 | 29 | 78 |
| 2 | 31 | 94 |
| 3 | 29 | 105 |
| 4 | 25 | 65 |

TABLE 6-continued

| Subject | Age (years) | Weight (kg) |
|---------|-------------|-------------|
| 5 | 31 | 81 |
| 6 | 25 | 75 |
| 7 | 53 | 76 |

Two days before treatment, a preliminary determination of maximal voluntary (isometric) contraction force (MVC) of knee extensors with the subject in the sitting position was carried out. MVC was determined using a Macflex system with subjects motivated by an instantaneous visual display of the force output. For each subject, two trials were carried out to determine endurance at 66% MVC sustained until the target force could no longer be maintained despite vocal encouragement. This first contraction was subsequently followed by a rest period of 60 seconds, with the subject remaining in the isometric chair. After the rest period, a second contraction was sustained to fatigue. Following a second rest of 60 seconds, a third contraction to fatigue was undertaken.

One day before treatment, the subjects reported to the isometric test laboratory between 8 and 10 am. MVC was determined and endurance at 66% MVC over three contractions with 60 second rest intervals, as described above, was determined. Measurements were determined using the subject's dominant leg. A biopsy of the lateral portion of the vastus lateralis was taken again from the dominant leg.

On day 1 of the treatment study, subjects reported to the blood sampling laboratory at 8 am following an overnight fast and a minimum of 12 hours since the last meat containing meal. Following catheterization and a basal blood sample, each subject followed the supplementation and blood sampling protocol described in Example 3. A dose of 10 milligrams per kilogram body weight of beta-alanine was administered at time 0 (9 am), 3 hours, and 6 hours.

On days 2–15, subjects continued to take three doses of 10 milligrams per kilogram body weight of beta-alanine.

In the morning of day 14, post-treatment isometric exercise tests were conducted on the dominant leg to determine MVC and endurance at 66% MVC relative to the 66% MVC measured on the day prior to treatment. In the afternoon, a muscle biopsy was taken of the vastus lateralis from close to the site of the biopsy taken on the day before treatment.

Figure 10:
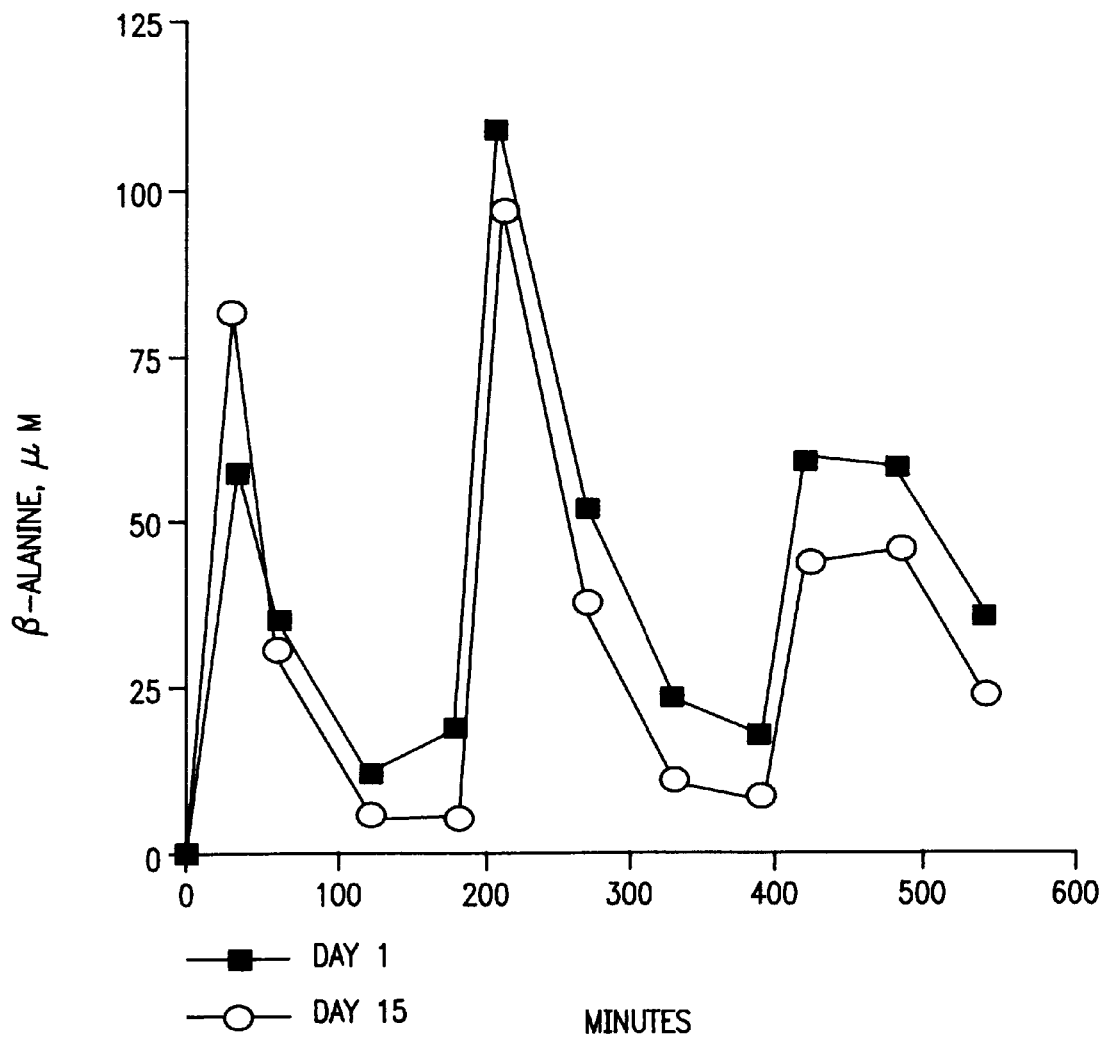
FIG. 10 is a graph depicting the mean changes in plasma beta-alanine over 9 hours following the oral ingestion of 10 milligrams per kilogram body weight of beta-alanine.
Figure 11:
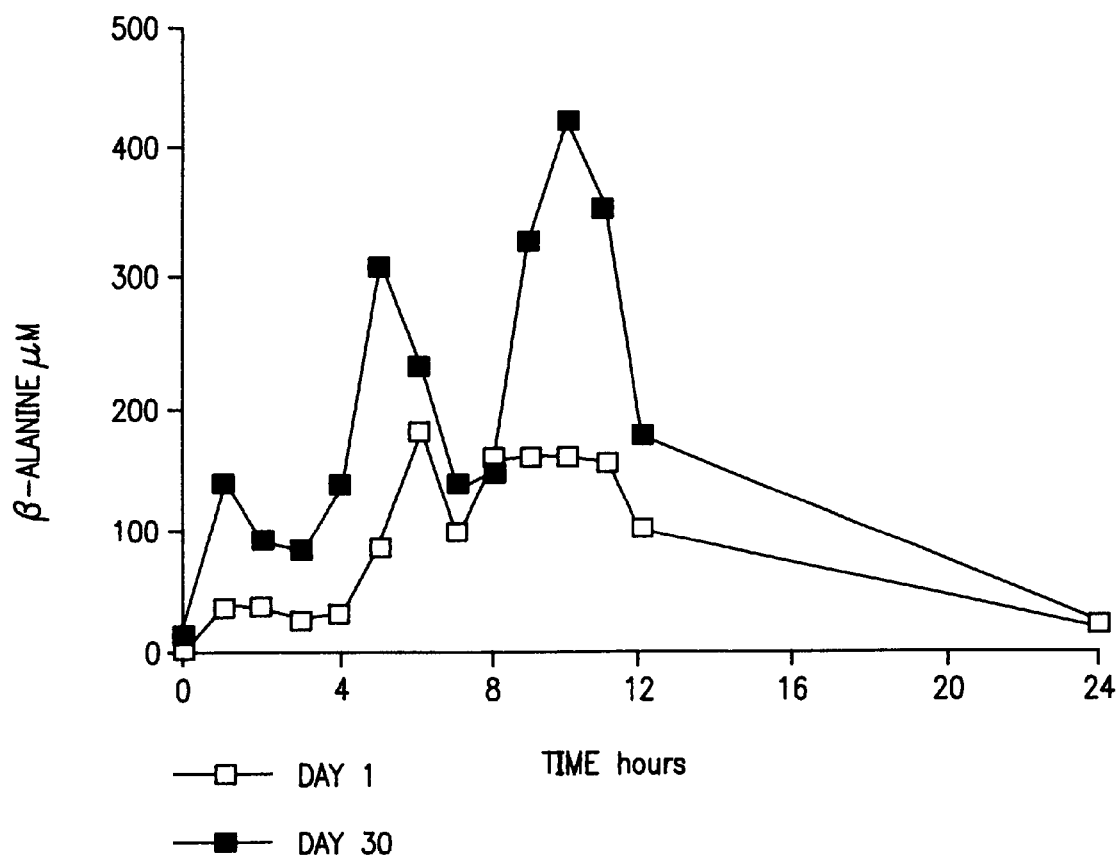
FIG. 11 is a graph depicting the mean (n=6) plasma beta-alanine concentration over the 24 hour of Day 1 and Day 30 of the treatment period.

On day 15, the procedures followed on day 1 were repeated to determine any overall shift in the plasma concentration profile of beta-alanine and taurine over the 15 days of supplementation. Mean changes in plasma beta-alanine over 9 hours following the oral ingestion of 10 milligrams per kilogram body weight of beta-alanine at 0, 3 and 6 hours on days 1 and 15 when dosing at 3×10 milligrams per kilogram body weight per day are shown in FIG. 10.

One additional test subject (number 7) followed the study, taking three doses 10 milligrams per kilogram body weight for 7 days followed by three doses of 20 milligrams per kilogram body weight for 7 days. No muscle biopsies were taken from this test subject.

There was no apparent change in the muscle carnosine content in the muscle of the six subjects biopsied. Changes in plasma taurine concentrations in the six subjects mirrored those of beta-alanine, as noted in Example 2.

Values from the MVC and endurance at 66% MVC measurements one day before treatment and after 14 days after treatment with three doses of 10 milligrams per kilogram body weight of beta-alanine are listed in Table 7. The mean endurance time at 66% MVC increased in 5 of the 6 subjects. An increase was also seen in subject 7 taking the higher dose.

TABLE 7

| Subject | MVC 1st try N | MVC 2nd try N | time @ 66% MVC 1st seconds | time @ 66% MVC 2nd seconds | time @ 66% MVC 3rd seconds | Total Contraction Time seconds |
|---------|---------------|---------------|---------------------------|---------------------------|---------------------------|-------------------------------|
| Pre | | | | | | |
| 1 | 784.5 | 821.9 | 48.53 | 29.03 | 23.78 | 100.83 |
| 2 | 814.4 | 886.2 | 48.40 | 26.03 | 16.90 | 91.33 |
| 3 | 984.9 | 970.4 | 38.15 | 26.03 | 16.78 | 80.95 |
| 4 | 714.6 | 740.4 | 89.03 | 56.15 | 45.65 | 190.83 |
| 5 | 1204.8 | 1217.2 | 37.65 | 27.64 | 21.53 | 86.83 |
| 6 | 722.4 | 716.8 | 46.78 | 29.40 | 21.90 | 98.08 |
| Pre mean | 870.9 | 892.1 | 51.4 | 32.4 | 24.3 | 108.1 |
| Pre SD | 190.6 | 184.6 | 19.1 | 11.7 | 10.8 | 41.2 |
| Post | | | | | | |
| 1 | 895.6 | 908.0 | 47.08 | 30.38 | 24.03 | 101.48 |
| 2 | 832.2 | 908.0 | 46.65 | 31.28 | 18.40 | 96.33 |
| 3 | 973.7 | 952.2 | 42.65 | 25.03 | 16.03 | 83.70 |
| 4 | 814.1 | 863.9 | 114.40 | 64.28 | 48.83 | 227.20 |
| 5 | 1246.6 | 1233.0 | 42.03 | 22.78 | 19.40 | 84.20 |
| 6 | 760.8 | 773.3 | 52.28 | 31.53 | 25.95 | 109.73 |
| Post mean | 920.5 | 939.7 | 57.5 | 34.2 | 25.4 | 117.1 |
| Post SD | 175.7 | 156.0 | 28.1 | 15.2 | 11.9 | 54.9 |
| Subject 7 | | | | | | |
| Pre | 858.18 | 861.54 | 54.0 | | | |
| Post | 792.54 | 851.41 | 62.0 | | | |

Other embodiments are within the claims.

What is claimed is:

1. A method of regulating hydronium ion concentrations in a human tissue comprising:

providing an amount of beta-alanine to blood or blood plasma effective to increase beta-alanylhistidine dipeptide synthesis in the human tissue; and exposing the tissue to the blood or blood plasma, whereby the concentration of beta-alanylhistidine is increased in the human tissue.

2. The method of claim 1, further comprising providing an amount of L-histidine to the blood or blood plasma effective to increase beta-alanylhistidine dipeptide synthesis in the human tissue.

3. The method of claim 1, further comprising increasing a concentration of creatine in the human tissue.

4. The method of claim 3, further comprising providing an amount of L-histidine to the blood or blood plasma effective to increase beta-alanylhistidine dipeptide synthesis in the human tissue.

5. The method of claim 3, wherein increasing the amount of creatine in the human tissue includes providing an amount of creatine to the blood or blood plasma effective to increase the concentration of creatine in the human tissue.

6. The method of claim 5, further comprising providing an amount of L-histidine to the blood or blood plasma effective to increase beta-alanylhistidine dipeptide synthesis in the human tissue.

7. The method of claim 1, wherein the providing step includes ingestion of a composition including the amount of beta-alanine.

8. The method of claim 1, wherein the providing step includes infusion of a composition including the amount of beta-alanine.

9. The method of claim 1, further comprising increasing a concentration of insulin in the blood or blood plasma.

10. The method of claim 9, further comprising providing an amount of L-histidine to the blood or blood plasma effective to increase beta-alanylhistidine dipeptide synthesis in the human tissue.

11. The method of claim 1, wherein the human tissue is a skeletal muscle.

* * * * *

UNITED STATES PATENT AND TRADEMARK OFFICE
CERTIFICATE OF CORRECTION

PATENT NO. : 5,965,596
DATED : October 12, 1999
INVENTOR(S) : Roger Harris and Mark Dunnett It is certified that error appears in the above-identified patent and that said Letters Patent is hereby corrected as shown below:

Column 1,
Line 43, delete the first occurrence of "formed".

Column 2,
Line 62, after "In" insert -- other --.

Signed and Sealed this

Eighteenth Day of May, 2004

JON W. DUDAS
*Acting Director of the United States Patent and Trademark Office*